United States Patent [19]

Tamm et al.

[11] Patent Number: 5,066,123

[45] Date of Patent: Nov. 19, 1991

[54] DEVICE FOR ELECTROTHERMAL ATOMIZING OF SAMPLES FOR SPECTROSCOPIC PURPOSES

[75] Inventors: Rolf Tamm, Salem; Gunther Rodel, Owingen; Erich Stengele, Taisersdorf, all of Fed. Rep. of Germany

[73] Assignee: Bodenseewerk Perkin Elmer GmbH, Überlingen, Fed. Rep. of Germany

[21] Appl. No.: 481,834

[22] Filed: Feb. 16, 1990

[30] Foreign Application Priority Data

Mar. 8, 1989 [DE] Fed. Rep. of Germany ....... 3907454

[51] Int. Cl.$^5$ ............................................ G01N 21/74
[52] U.S. Cl. ..................................... 356/312; 356/244
[58] Field of Search ................................. 356/312, 244

[56] References Cited

U.S. PATENT DOCUMENTS

| | | | |
|---|---|---|---|
| 3,895,873 | 7/1975 | Dennison et al. | 356/312 |
| 4,443,105 | 4/1984 | Huber et al. | 356/312 |
| 4,639,136 | 1/1987 | Morton | 356/312 |
| 4,721,387 | 1/1988 | Brown | 356/312 |
| 4,824,241 | 4/1989 | Littlejohn et al. | 356/312 |

Primary Examiner—F. L. Evans
Attorney, Agent, or Firm—Thomas P. Murphy; Edwin T. Grimes

[57] ABSTRACT

A device for electrothermal atomization of samples for spectroscopic purposes with a furnace body made of graphite, designed such that electrical current can be passed through, and a pot-shaped sample receptacle which is separated from the furnace body and projects into a lateral aperture of the furnace body comprises a driving device by which the sample receptacle is movable into and out of thermal contact with the furnace body. The driving device together with the heating current of the furnace body is controlled by a controlling device such that the sample receptacle engages the furnace body during a drying and decomposing step and thereafter, is raised from the furnace body by the driving device. Thereafter, with raised sample receptacle, the furnace body is heated to atomization temperature until a temperature stabilization is achieved and, finally, the sample receptacle is again moved into contact with the furnace body.

4 Claims, 2 Drawing Sheets

DEVICE FOR ELECTROTHERMAL ATOMIZING OF SAMPLES FOR SPECTROSCOPIC PURPOSES

TECHNICAL FIELD

The invention relates to a furnace for electrothermal atomization of samples for spectroscopic purposes. Such a furnace comprises:

a furnace body made of an electrically conductive, spectroscopically inert material;

means for passing electrical current through this furnace body;

a sample receptacle which is separated from the furnace body and projects into a lateral aperture of the furnace body.

BACKGROUND OF THE INVENTION

The invention is particularly useful in the atomic absorption spectroscopy; that is, a method for determining the amount of concentration of a looked-for element in a sample. An atomizing device generates an "atom vapor" wherein the components of the sample are present in an atomic state. A measuring light beam from a line-emitting light source, a hollow cathode lamp, for example, is passed through this atom vapor. The spectral lines which are present in the measuring light beam correspond to the resonant lines of a looked-for element the amount or concentration of which shall be determined in the sample. The measuring light beam undergoes an absorption which is determined by the amount or concentration of the looked-for element. Ideally, the measuring light beam is not influenced by the atoms of the other elements which are present in the sample. The fact is used that atoms absorb only such wavelengths from a measuring light beam which they emit with a corresponding excitation in the light source. The attenuation of the measuring light beam in the atom vapor is measured by means of a detector and provides a measure for the looked-for amount or concentration.

It is known to atomize the sample electrothermally. For this purpose, the sample is inserted into a furnace with a furnace body made of graphite. A high electrical current is passed through the furnace body such that the furnace body is heated to a high temperature. Then, a "cloud of atoms" or atomic vapor is generated in the furnace body. The furnace body has a passage through which the measuring light beam is directed such that it passes through the "cloud of atoms".

In a conventional embodiment the furnace body is a graphite tube which is held between two annular contacts. The measuring light beam passes longitudinally through the contacts and the bore of the graphite tube. The sample, mostly present as a solution, is inserted through a lateral aperture into the graphite tube (DE-PS 24 13 781).

The current through and, therefore, the temperature of the graphite tub is modified according to a certain program. At first, the sample is dried at a relatively low temperature, i.e., the solvent is vaporized. Then, in a second step, the remaining sample substance is ashed or decomposed. Finally, the graphite tube is heated to a high atomization temperature, the measurement taking place.

There are furnaces for the electrothermal atomization also known in which current flows through lateral contact elements peripherally around a tubular furnace body (U.S. Pat. No. 4,407,582, DE-OS 35 34 417, Analytical Chemistry 58 (1986), 1973).

It is desired to delay the atomization of the sample relative to the heating of the furnace until there is a constant temperature condition, i.e., the inner wall of the furnace body has achieved its final temperature. Different measures are known by which such a delay is achieved.

It is known to provide in a device for electrothermal atomization of samples a sample carrier separated from the furnace body which projects into a lateral aperture of the furnace body and is heated separately from the furnace body. Then, the furnace body can first be heated to its equilibrium temperature before the heating of the sample carrier is switched on.

Furthermore, it is known to use a sample carrier designed as a small platform in a furnace body designed as a graphite tube. The platform is heated by the heated furnace body substantially indirectly through the radiation emitted by the walls of the furnace body such that the heating of the sample is delayed relative to the heating of the furnace body ("Spectrochimica Acta", 33B (1978), 153-193).

However, the small platform can only accommodate a correspondingly small amount of sample. Therefore, a sample carrier designed as a platform is known which can be inserted into a furnace body designed as a graphite tube, the sample carrier having a recess for accommodating the sample and only being guided into the furnace body along two opposite longitudinal edges (German patent 29 24 123, Company Publication "Variation GTA-96, Graphite Tube Atomizer")

U.S. Pat. No. 3,895,873 describes an atomizing device for electrothermal atomization of samples for atomic absorption spectroscopy in which a furnace body of a square cross-section has a lateral slot in a vertical lateral wall above its lower, horizontal lateral wall. This lateral slot is arranged such that a sample carrier having a recess for accommodating the sample can be inserted into it. When the sample carrier is inserted it comes into close thermal contact to the furnace body. Before the heating up of the furnace body the sample carrier is manually inserted by means of a tool.

British Patent 2,144,871 shows a similar arrangement in which a sample carrier can be inserted into a furnace body designed as a graphite tube through a lateral slot. The sample carrier is inserted before the heating up of the furnace body and is not in heat-conductive contact with the wall of the furnace body.

U.S. Pat. No. 4,202,628 shows a device for electrothermal atomization of samples in which a furnace body designed as a graphite tube has in its center a pot-shaped recess which accommodates the sample. However, this pot-shaped recess is integral with the graphite tube, the heating current constantly flows through both tube and recess. The electrical resistance of the recess is smaller than that of the other graphite tube such that the temperature of the pot-shaped recess is smaller than that of the other graphite tube. Thereby, it shall be achieved that the main portion of the generated atom vapor is in an "absorption cell element" above the recess. This is also true for the stationary condition.

German Patent 23 23 774 shows a furnace body designed as a graphite tube in which the inner wall of the furnace body is provided with slots or a thread. Thereby, the spreading of a sample to the ends of the graphite tube is counteracted.

From German Patent 32 04 873 a device for automatic insertion of a sample into the furnace of an automatic absorption spectrometer is known. In this device a sample carrier is longitudinally inserted into the furnace space of the furnace body by means of a program-controlled gripping device. A plurality of sample carriers is arranged in a movable sample carrier holder and they are consecutively conveyed into the area of the gripping device.

DISCLOSURE OF THE INVENTION

The object of the invention is to design a device of the type defined above in order to atomize a sample for spectroscopic purposes such that:

The atomization of the sample is delayed relative to the heating of the furnace body such that the furnace body has substantially reached its equilibrium temperature by the time the sample is atomized, a large amount of the sample can be charged, and only one heating is required for the atomization of the sample and for the furnace body.

In addition, the device shall facilitate the automation of the sample charging such that, with a simple design different samples can be consecutively inserted into the device and can be atomized.

According to the invention this object is achieved in that:

the sample receptacle is movable into and out of thermal contact with the furnace body by a driving device.

The sample receptacle can be a pot. Thereby, large amounts of the sample can be charged. The driving device can be controlled together with the heating current of the furnace body by control means such that the sample receptacle engages the furnace body during a drying and decomposing step, and thereafter, is removed for the furnace body by the driving mechanism. Subsequently, the furnace body with the sample receptacle removed, is heated to atomization temperature until a temperature stabilization is achieved, and finally, the sample receptacle is again moved into contact with the furnace body by the driving device. The driving mechanism can be connected with the sample receptacle by a poorly heat-conductive connecting member. This connecting member can be a rod made of a poorly heat-conductive material through which the driving device engages the sample receptacle and which is movable by the driving device longitudinally to the rod. For further reduction of the heat dissipation from the sample receptacle the rod can be provided with at least one contraction. The driving device can be formed by a fluid actuated jack or a solenoid.

The invention offers the possibility that sample receptacles with different samples can be consecutively moved by a conveying device into the area of the driving device and the driving device consecutively raises the sample receptacles from the conveying device and moves them into contact with the furnace body.

An embodiment of the invention will now be described in further detail with reference to the accompanying drawings.

PREFERRED EMBODIMENT OF THE INVENTION

Figure 1:
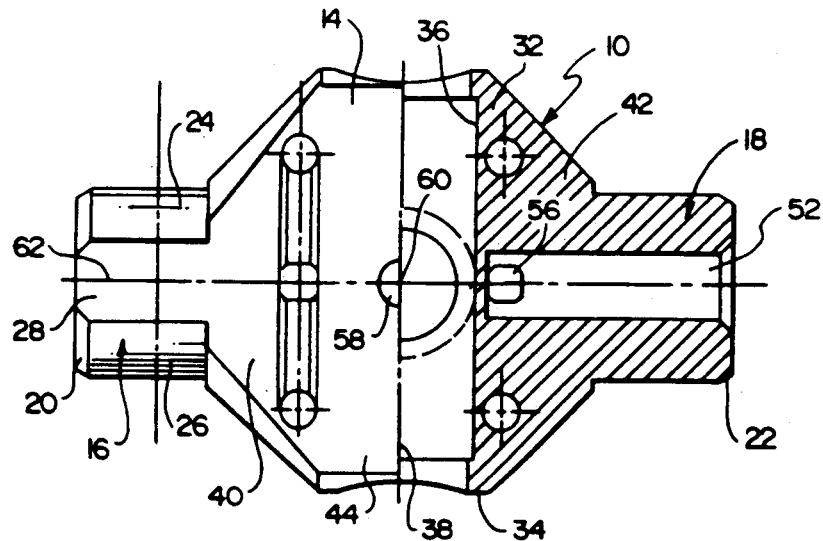
FIG. 1 shows a partially sectional plan view of a furnace in a device for atomizing a sample in atomic absorption spectroscopy.
Figure 2:
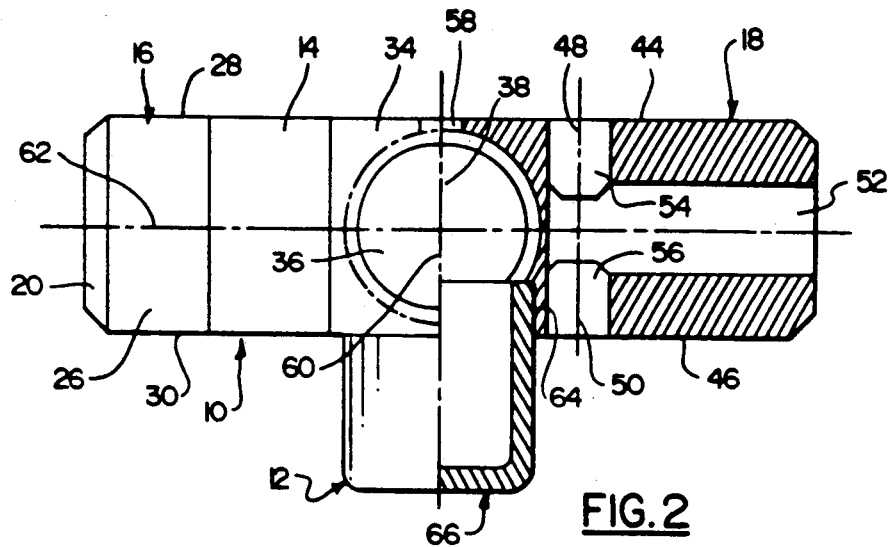
FIG. 2 shows a lateral elevation of the furnace, also in a partially sectional view.

FIGS. 1 and 2 illustrate a furnace with a furnace body 10 made of graphite and a sample receptacle 12 having the shape of a pot. The sample receptacle 12 is also made of graphite.

The furnace body 10 is made of a plate and has a center portion 14 which has a generally octagonal shape in plan view. At their ends the contact elements 16 and 18 have conical contact surfaces 20 and 22, respectively. As can be seen in the left part of FIG. 1, the contact elements, e.g., contact element 16, have cylindrical peripheral surfaces 24 and 26 which are interconnected by plane surfaces 28 and 30. These plane surfaces 28 and 30 form a part of the planar surfaces of the plate from which the furnace body 10 is formed. The two opposite side faces 32 and 34 of the octagonal center portion 14, which extend perpendicular to the side faces supporting the contact elements 16 and 18, communicate through a bore 36. The bore 36 forms the interior cavity of the furnace body 10. In operation, the measuring light beam of the atomic absorption spectrometer passes through the bore 36 along the axis 38 of the bore.

The other transversely extending side faces of the center portion 14 form trapezoidal contact elements 40 and 42 between the furnace portion 44 comprising the bore 36 and the contact elements 16 and 18. In the contact elements 40 and 42, e.g., the contact element 42, slots 48 and 50, respectively, are provided parallel to the axis 38 of the bore 36 in the two plane surfaces 44 and 46 of the plate. The slots 48 and 50 form contractions of the contact elements 40 and 42, respectively, and counteract the dissipation of heat from the furnace section 44. Longitudinal passages 52 extend in the contact elements 40 and 42 and in the contact pieces 16 and 18, e,g., in the contact element 42 and the contact piece 18. As can be seen in FIG. 2, the longitudinal passages 52 cut the slots 48 and 50 such that passages 54 and 56, respectively are formed. A bore 58 is provided in the center of the center portion 14 in the plane surface 44. The bore 58 communicates with the bore 36.

The axis of this bore 58 is designated by numeral 60. The axis of the contact pieces 16 and 18 and the bore 52 is designated by numeral 62. The axes 38, 60 and 62 meet in one point and are perpendicular to each other.

A flat cylindrical recess 64 is formed in the plane surface 46 on the side opposite of the bore 58. The recess 64 cuts the bore 36 as can be best seen in FIG. 2. A pot-shaped sample receptacle 66 made of graphite can be inserted into this recess 64. Then the rims of the pot-shaped sample receptacle 66 are in heat conductive contact with the furnace body 10.

Figure 4:
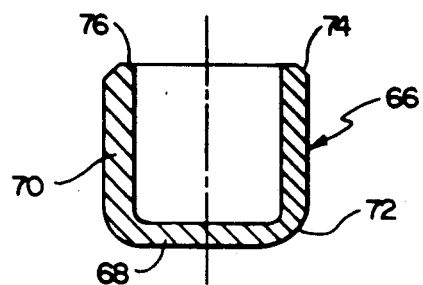
FIG. 4 shows a section taken through the sample receptacle.
Figure 5:
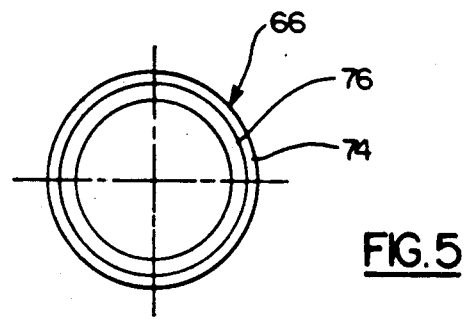
FIG. 5 shows a plan view of the sample receptacle.

The sample receptacle 66 is illustrated in detail in FIGS. 4 and 5.

The sample receptacle 66 forms a pot with a bottom 68 and a cylindrical side wall 70. The bottom 68 is connected to the side wall 70 through a rounded edge 72. A conical surface 74 is formed at the outside of the end face of the side wall 70 adjacent to which conical surface extends a plane ring surface 76. The conical surface facilitates the insertion of the upper rim of the side wall 70 into the recess 64 of the furnace body 10. The plane ring surface 76 ensures safe contact with the plane surfaces of the furnace body 10 formed at the bottom of the recess 64 on both sides of the bore 36.

Figure 3:
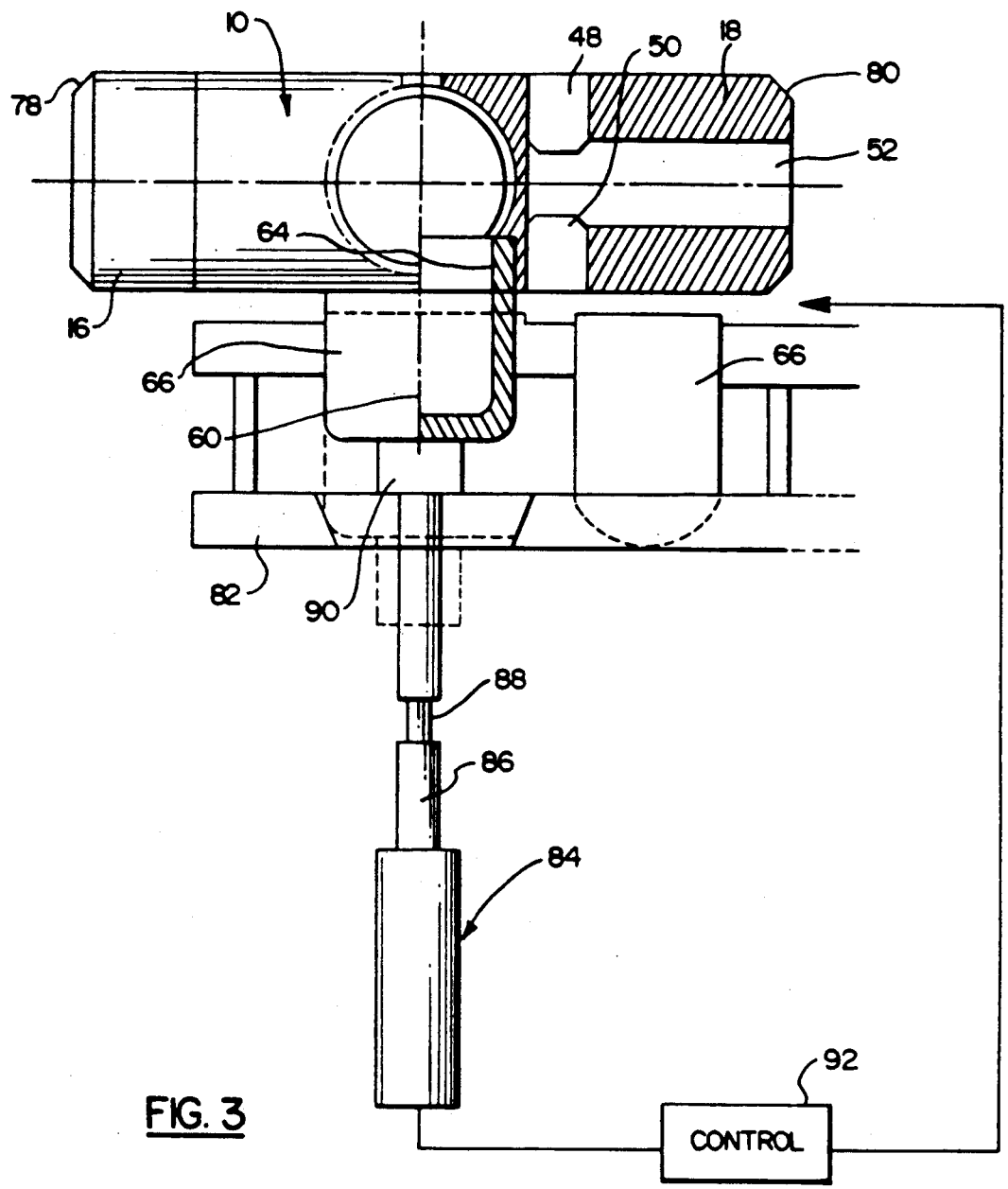
FIG. 3 shows the lateral elevation of the furnace similar to FIG. 2 together with a driving mechanism for the sample receptacle illustrated schematically, and a conveying device also illustrated schematically as a turntable for a plurality of sample receptacles.

FIG. 3 shows schematically the described furnace in operation.

The furnace body 10 is held with its contact elements 16 and 18 and the conical contact surfaces 20 and 22, respectively, between housing fixed contacts 78 and 80, respectively. The contacts 78 and 80 are also made of graphite and are illustrated only schematically. The turntable 82 or another conveying device operating similarly extends up to and under the furnace body 10. A plurality of sample receptacles 66 of the type illustrated in FIGS. 4 and 5 are held in the turntable 82. In the rest position the sample receptacles 66 are spaced below the furnace body 10, as illustrated in FIG. 3 by broken lines. In this position, the sample receptacles 66 are neither in electrical contact nor in heat conductive contact with the furnace body. In the different operational positions of the turntable one of the sample receptacles 66 are neither in electrical contact nor in heat conductive contact with the furnace body. In the different operational positions of the turntable one of the sample receptacles 66 is aligned with the recess 64 of the furnace body 10.

Now, the pot-shaped sample receptacle 66 can be lifted from the turntable 82 and can be pressed into the recess 64 by a driving device 84. This driving device 84 can be a fluid actuated jack or a solenoid. So that there is no undesired heat dissipation from the sample receptacle 66 caused by the contact between driving device 84 and sample receptacle 66, the driving device 84 engages the pot-shaped sample receptacle 66 through a rod 86 made of a poorly heat-conductive material. The rod 86 extends in the lifting direction of the driving device 84. When the driving device 84 is a jack, for example, the rod 86 forms the piston rod of the jack or an extension thereof. In order to further reduce the heat dissipation, the rod 86 is provided by a contraction 88. At the furnace-side end the rod 86 is provided with a disc 90. The rod 86 and the rotational axis of the turntable 82 are parallel to the axis 60 of the furnace. The disc 90 engages the bottom 68 of the pot-shaped sample receptacle 66 and lifts the sample receptacle relative to the turntable 82 and presses it into the recess 64 of the furnace body 10. Then, through the ring surface 76, a close electrical and heat-conductive contact between sample receptacle 66 and furnace body 10 is achieved.

The driving device 84 as well as the current which is passed through the contacts 78 and 80 through the furnace body 10, can be controlled by a controlling device 92, as indicated in FIG. 3.

The described arrangement operates as follows:

Samples to be analyzed are put into the sample receptacles 66. The sample receptacles 66 are inserted into the turntable. One after the other, the different sample receptacles are brought to their operational position below the furnace body 10.

The driving device 84 brings the sample receptacle 66 with this ring surface 76 into engagement with the plane surface at the bottom of the recess 64. Then, an electrical current is passed through the contacts 78 and 80 through the furnace body 10 which first heats the furnace body to a drying temperature and then heats it to an ashing temperature. In addition, an inert gas flow is supplied through the contacts 78 and 80 and the passages 52. This inert gas flow is distributed around the furnace body through the grooves 48 and 50. The inert gas also enters the bore 36. This partial flow emerges through the bore 58 and carries away drying and ashing products. During this process not only is the sample receptacle 66 in heat-conductive contact with the furnace body 10, but since a part of the electrical current flows through the sample receptacle Joul's heat is also generated within the sample receptacle itself.

After the drying and ashing process the sample receptacle is again lowered. Then, it is arranged at a distance below the furnace body 10, as indicated in FIG. 3 by broken lines. At this time, a strong current flows through the furnace body 10 and the furnace body is heated to atomization temperature. In the beginning, the sample receptacle 66 is substantially not influenced thereby. However, when the furnace body has reached a state of equilibrium and all portions of the wall have attained atomization temperature, the sample receptacle is again lifted. It is moved into the recess 64 and regains heat-conductive contact with the furnace body. Now, the atomization of the sample and the generation of the "cloud of atoms" is effected in the known manner. However, this is made with a defined delay relative to the heating up of the furnace body 10.

By the described arrangement different advantages are achieved at the same time.

Large amounts of a sample can be atomized.

The atomization of the sample is made with a well-defined delay relative to the heating up of the furnace body to atomization temperature.

An automation of the analysis of a plurality of samples can be achieved with quite simple means in that different sample receptacles are consecutively moved under the furnace body by a turntable and are pressed against the furnace body by means of a driving device.

What is claimed is:

1. In a device for electrothermal atomization of samples for spectroscopic purposes, comprising:
   a furnace body made of an electrically conductive, spectroscopically inert material,
   means for passing electrical current through the furnace body,
   a sample receptacle comprising a pot which is separated from the furnace body and projects into a lateral aperture of the furnace body,
   a rod made of thermally insulating material and comprising at least one contraction,
   a driving device connected to said sample receptacle via said rod for moving said pot into and out of thermal contact with the furnace body,
   a controlling device for controlling the driving device and the electrical heating current through the furnace body, for causing said sample receptacle to engage said furnace body during a drying and decomposing step and thereafter to be removed from the furnace body by said driving device, and with said sample receptacle removed, for causing said furnace body to be heated to an atomization temperature, and then moved into contact with said sample receptacle.

2. A device as set forth in claim 1 wherein said driving device comprises a fluid actuated jack.

3. A device as set forth in claim 1 characterized said driving device comprises a solenoid.

4. A device as set forth in claim 3 further comprises:
   conveying means, said conveying means holding a plurality of sample receptacles and consecutively moving said sample receptacles into an activation area of said driving device wherein said driving device consecutively raises said sample receptacles from said conveying means and moves them into contact with said furnace body.

* * * * *